United States Patent
Nobori et al.

(10) Patent No.: US 6,469,224 B1
(45) Date of Patent: Oct. 22, 2002

(54) PROCESS FOR PREPARATION OF SUBSTITUTED AROMATIC COMPOUND

(75) Inventors: Tadahito Nobori, Chiba (JP); Setsuko Fujiyoshi, Chiba (JP); Isao Hara, Chiba (JP); Takaomi Hayashi, Chiba (JP); Atsushi Shibahara, Tokyo (JP); Katsuhiko Funaki, Chiba (JP); Kazumi Mizutani, Chiba (JP); Shinji Kiyono, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 10/018,424

(22) PCT Filed: Apr. 20, 2001

(86) PCT No.: PCT/JP01/03392
§ 371 (c)(1), (2), (4) Date: Dec. 20, 2001

(87) PCT Pub. No.: WO01/81274
PCT Pub. Date: Nov. 1, 2001

(51) Int. Cl.[7] ............ C07B 39/00; C07C 17/20; C07C 25/13; C07C 253/14; C07D 209/08
(52) U.S. Cl. ............ 585/400; 546/345; 548/491; 568/10
(58) Field of Search ............ 546/345; 548/491; 568/10; 585/400

(56) References Cited

FOREIGN PATENT DOCUMENTS

EP        0 791 600 A1        8/1997

OTHER PUBLICATIONS

Database CAPLUS on STN, Acc. No. 1988:37964, Schwesinger et al., Angew. Chem. (1987), 99(11), p. 1212–14 (abstract).*
Database CAPLUS on STN, Acc. No. 1992:6651, Schwesinger et al., Angew. Chem.(1991), 103(10), p. 1376–8 (abstract).*
Schwesinger, R. et al., "Stable phosphazenium ions in synthesis—an easily accessible, extremely reactive 'naked' fluoride salt.", Angew. Chem., Int. Ed. Engl., vol. 30, No. 10 (1991) pp. 1372–1375.

* cited by examiner

Primary Examiner—Brian J. Davis
(74) Attorney, Agent, or Firm—Burns Doane Swecker & Mathis LLP

(57) ABSTRACT

A substituted aromatic compound substituted with Q is obtained by reacting a phosphazenium compound represented by formula (1)

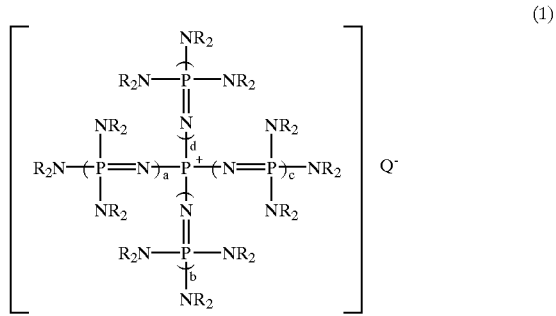

(in the formula, $Q^-$ represents an anion in a form derived by elimination of a proton from an inorganic acid, or an active hydrogen compound having an active hydrogen on an oxygen atom, a nitrogen atom or a sulfur atom; a, b, c and d, each independently, is 0 or 1, but all of them are not 0 simultaneously; and R groups represent the same or different hydrocarbon groups having 1 to 10 carbon atoms, or two Rs on each common nitrogen atom may be bonded together to form a ring structure) with a halogenated aromatic compound having halogen atoms; whereby, at least one halogen atom in the halogenated aromatic compound is substituted with Q (where, Q represents an inorganic group or an organic group in a form derived by elimination of one electron from $Q^-$ in formula (1)).

17 Claims, 1 Drawing Sheet

● Example 21
▲ Comparative Example 1
■ Comparative Example 2
◆ Comparative Example 3

PROCESS FOR PREPARATION OF SUBSTITUTED AROMATIC COMPOUND

TECHNICAL FIELD

The present invention relates to a process for preparation of substituted aromatic compounds that are useful as products or intermediates for industrial chemicals, polymers, medical and agricultural chemicals and others, using halogenated aromatic compounds, especially chlorinated aromatic compounds that are industrially producible and available at a low price as starting materials and by substituting the chlorine atom of the above described chlorinated compounds with various nucleophilic substances.

BACKGROUND ART

As one method for producing substituted aromatic compounds, a nucleophilic substitution reaction of aromatics is known in which a halogenated aromatic compound is reacted with a nucleophilic agent to substitute the above described halogen atom with the nucleophilic species, but it is also known that generally a halogenated aromatic compound has remarkably low reactivity to a nucleophilic species as compared to a aliphatic halogenated compound. However, if a specific substituent exists at a specific position of an aromatic ring as in p-nitrochlorobenzene, 2,4-dinitrochlorobenzene, or p-benzoylchlorobenzene (active halogenated aromatic compounds), the halogen atoms of the halogenated aromatic compounds is remarkably activated to the nucleophilic substitution reaction by the substituent to progress easily the reaction.

On the other hand, as described in "Organic Chemistry (the last volume, Japanese version)", 5th edition, written by R. T. Morrison and R. N. Boyd, page 1289 that "it will end in failure even if a halogenated aryl compound (this is an inactive halogenated aromatic compound in the present invention) or a halogenated vinyl compound is tried to be treated with a usual nucleophilic reaction agent to convert phenol, ether, amine or nitrile", it is described each in the following literatures that an inactive halogenated aromatic compound, such as chlorobenzene, p-bromobenzene, o-methoxyiodobenzene or the like, in which no such a substituent exists does not react with a nucleophilic agent unless ① the reaction is carried out in very severe reaction conditions, or ② once the halogen atom in the halogenated compound is activated by making it an organic metal complex in which the aromatic ring is a ligand, or ③ a catalyst is made to exist: ① Fyfe, in Patai, "The Chemistry of the Hydroxy Group," pt.1, pp.83–124, Interscience Publishers, Inc., New York, 1971; ② Semmelhack and Hall, J. Am. Chem. Soc., 96, 7091, 7092 (1974); M. Fukui, Y. Endo and T. Oishi, Chem. Pharm. Bull., 28, 3639 (1980); or ③ A. A. Moroz and M. S. Shvartsberg, Russ. Chem. Rev. 43, 679–689 (1974); Mowry, Chem. Rev., 42, 189–283 (1948), pp207–209; S. L. Buchwald et al., J. Am. Chem. Soc., 119, 10539–10540 (1997); S. L. Buchwald et al., J. Am. Chem. Soc., 122, 1360–1370 (2000).

Among inactive halogenated aromatic compounds, in particular, chlorinated aromatic compounds have extremely low reactivity as compared to corresponding halogenated aromatic compounds of non-chlorinated series and no effective reaction agent or catalyst have been available. However, because the above described chlorinated compounds are industrially producible and available at a low price, recently, various kinds of reaction agents and catalysts have been developed to achieve the nucleophilic substitution reaction of inactive chlorinated aromatic compounds. For example, in L. I. Goryunov and V. D. Shteingarts, Russ. J. Org. Chem., 29, 1849–1855 (1993), it is disclosed that using Rh complex, which is expensive and difficult to be industrially produced, as a catalyst and chlorobenzene as a raw material, methoxybenzene can be obtained in the yield of 60 to 75% by reacting the chlorobenzene at reaction temperature between 80° C. and 180° C. for 4 days to 1 hour. In U.S. Pat. No. 5,315,043 or U.S. Pat. No. 6,087,543, it is disclosed that a specific fluorination reagent are reacted with chlorobenzene under very severe conditions of at a temperature between 210° C. and 450° C. to produce fluorobenzene in the yield of 6 to 70%.

DISCLOSURE OF INVENTION

An object of the present invention is to provide an effective method to produce substituted aromatic compounds from halogenated aromatic compounds, especially chlorinated aromatic compounds, with high yield under mild reaction conditions by using reaction reagents which are extremely effective to the nucleophilic substitution reaction.

Accordingly, the present invention is a process for preparation of a substituted aromatic compound substituted with Q, which comprises:

reacting a phosphazenium compound represented by formula (1)

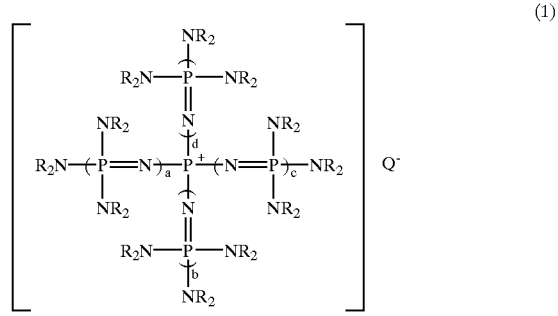

(in the formula, $Q^-$ represents an anion in a form derived by elimination of a proton from an inorganic acid, or an active hydrogen compound having an active hydrogen on an oxygen atom, a nitrogen atom or a sulfur atom; a, b, c and d, each independently, is 0 or 1, but all of them are not 0 simultaneously; and R groups represent the same or different hydrocarbon groups having 1 to 10 carbon atoms, or two Rs on each common nitrogen atom may be bonded together to form a ring structure) with a halogenated aromatic compound having halogen atoms; whereby, at least one halogen atom in the halogenated aromatic compound is substituted with Q (where, Q represents an inorganic group or an organic group in a form derived by elimination of one electron from Q in formula (1)).

The present inventors have earnestly studied for the purpose of providing a method of industrially favorably producing substituted aromatic compounds, resulting in finding that the reactivity of various nucleophilic anion species represented by $Q^-$ in formula (1) to the nucleophilic substitution reaction of aromatics is drastically improved by the use of a phosphazenium cation in formula (1) as a counter cation. The inventors found that with the use of phosphazenium compounds represented by formula (1), the nucleophilic substitution reaction of inactive halogenated aromatic compounds, especially inactive chlorinated aromatic compounds, which had been conventionally considered to be difficult, could be progressed under extremely mild conditions and objective substituted aromatic compounds could be obtained in high yields. As a result, the present invention is completed.

To be concrete, for example, as shown in Example 1 and Example 2 to be described later, it has been found surprisingly that tetrakis[tris(dimethylamino)phosphoranylideneamino]phosphonium methoxide: $[(Me_2N)_3P=N]_4P^+$, $MeO^-$ (Me represents methyl group in the formula and the following description) easily reacts with chlorobenzene at room temperature to produce desired methoxybenzene in the yield of 95%, and that when tetrakis[tris(dimethylamino)phosphoranylideneamino]phosphonium fluoride: $[(Me_2N)_3P=N]_4P^+$, $F^-$ is used, it reacts with chlorobenzene under an extremely mild condition of 130° C. compared to the conventional condition to produce fluorobenzene in the yield of 81%.

Further, in one aspect of the present invention, when a substitution reaction with $Q^-$ is carried out, a phosphazenium compound represented by formula (2)

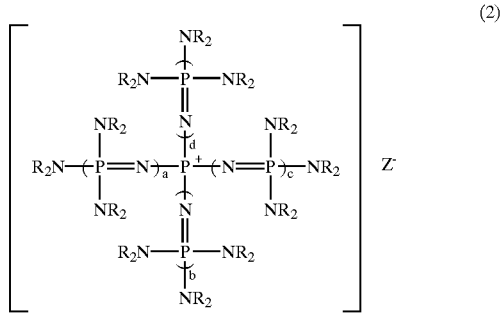

(2)

(in the formula, $Z^-$ is a halogen anion, and a, b, c, d and R groups are the same meaning as described above) and a metal compound represented by $MQ_n$ (in the formula, M represents an alkaline metal atom, an alkaline earth metal atom, or a rare earth metal atom, Q is the same meaning as described above, and n is an integer from 1 to 3) are used as raw materials and made contact with each other to produce a phosphazenium compound represented by the above described formula (1) in the reaction system, and thus the above described substitution reaction can be carried out.

BEST MODE FOR CARRYING OUT THE INVENTION

Figure 1:
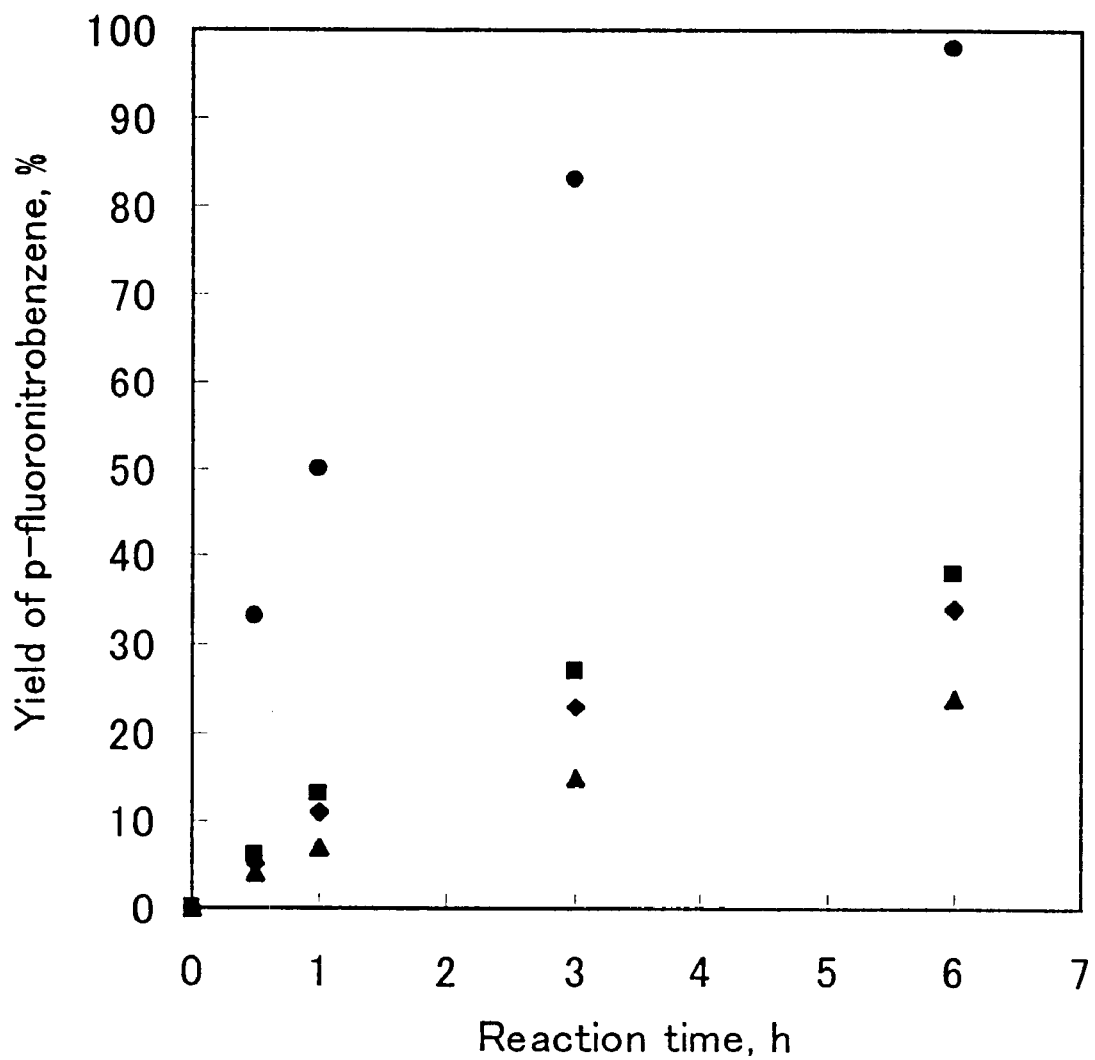
FIG. 1 is a graph showing the reaction rates of p-fluoronitrobenzene in Example 21 and Comparative examples 1 to 3.

Although phosphazenium compounds of formula (1) or (2) that are used in the present invention are representatively expressed by a canonical formula (that is, formula (1) or formula (2)) in which a positive charge of phosphazenium cation is localized on a central phosphorus atom, an infinite number of canonical formulas other than this formula can be depicted and positive charge is actually nonlocalized entirely.

Among compounds from which anionic $Q^-$ is derived, examples of inorganic acids include: hydrogen halides, including, for example, hydrogen fluoride, hydrogen chloride, hydrogen bromide or hydrogen iodide; hydrogen cyanide; thiocyanic acid; hydrogen azide or the like.

Among compounds from which anionic $Q^-$ is derived, examples of active compounds having active hydrogen atoms on oxygen atom include: water; carboxylic acids having 1 to 20 carbon atoms, including, for example, formic acid, acetic acid, propionic acid, butyric acid, isobutyric acid, lauric acid, stearic acid, oleic acid, phenylacetic acid, dihydrocinnamic acid, cyclohexanecarboxylic acid, benzoic acid, paramethylbenzoic acid and 2-carboxynaphthalene; polyvalent carboxylic acids having 2 to 20 carbon atoms having 2 to 6 carboxyl groups, including, for example, oxalic acid, malonic acid, succinic acid, maleic acid, fumaric acid, adipic acid, itaconic acid, butanetetracarboxylic acid, phthalic acid, isophthalic acid, terephthalic acid, trimellitic acid and pyromellitic acid; carbamic acids including, for example, N,N-diethylcarbamic acid, N-carboxypyrrolidone, N-carboxyaniline and N,N'-dicarboxy-2,4-toluenediamine; alcohols having 1 to 20 carbon atoms, including, for example, methanol, ethanol, normal propanol, isopropanol, normal butyl alcohol, secondary butyl alcohol, tertiary butyl alcohol, isopentyl alcohol, tertiary pentyl alcohol, normal octyl alcohol, lauryl alcohol, cetyl alcohol, cyclopentanol, cyclohexanol, allyl alcohol, crotyl alcohol, methyl vinyl carbinol, benzyl alcohol, 1-phenylethyl alcohol, triphenyl carbinol and cinnamic alcohol; polyhydric alcohols having 2 to 20 carbon atoms and 2 to 8 hydroxyl groups, including, for example, ethylene glycol, propylene glycol, diethylene glycol, dipropylene glycol, 1,3-propanediol, 1,3-butanediol, 1,4-butanediol, 1,6-hexanediol, 1,4-cyclohexanediol, trimethylolpropane, glycerin, diglycerin, pentaerythritol and dipentaerythritol; aromatic compounds having 6 to 20 carbon atoms and 1 to 3 hydroxyl groups, including, for example, phenol, 2-naphthol, 2,6-dihydroxynaphthalene and bisphenol A; and others.

Among compounds from which anionic $Q^-$ is derived, examples of active hydrogen compounds having active hydrogen atoms on nitrogenatominclude: aliphatic or aromatic primary amines having 1 to 20 carbon atoms, including, for example, methylamine, ethylamine, normal propylamine, isopropylamine, normal butylamine, isobutylamine, secondary butylamine, tertiary butylamine, cyclohexylamine, benzylamine, β-phenylethylamine, aniline, o-toluidine, m-toluidine and p-toluidine; aliphatic or aromatic secondary amines having 2 to 20 carbon atoms, including, for example, dimethylamine, methylethylamine, diethylamine, di-normal-propylamine, ethyl-normal-butylamine, methyl-secondary-butylamine, dipentylamine, dicyclohexylamine, N-methylaniline and diphenylamine; polyvalent amines having 2 to 20 carbon atoms and 2 to 3 primary or secondary amino groups, including, for example, ethylenediamine, di(2-aminoethyl)amine, hexamethylenediamine, 4,4'-diaminodiphenylmethane, tri(2-aminoethyl)amine, N,N'-dimethylethylenediamine, N,N'-diethylethylenediamine and di(2-methylaminoethyl)amine; saturated cyclic secondary amines having 4 to 20 carbon atoms, including, for example, pyrrolidine, piperidine, morpholine and 1,2,3,4-tetrahydroquinoline; unsaturated cyclic secondary amines having 4 to 20 carbon atoms, including, for example, 3-pyrroline, pyrrole, indole, carbazole, imidazole, pyrazole and purine; cyclic polyvalent amines having 4 to 20 carbon atoms and 2 to 3 secondary amino groups, including, for example, piperazine, pyrazine and 1,4,7-triazacyclononane; nonsubstituted or N-monosubstituted acid amides having 2 to 20 carbon atoms, including, for example, acetamide, propionamide, N-methyl propionamide, N-methylbenzoic acid amide and N-ethylstearic acid amide; cyclic amides of five to seven-membered rings, including, for example, 2-pyrrolidone and ε-caprolactam; imides of dicarboxylic acids having 4 to 10 carbon atoms, including, for example, succinimide, maleinimide and phthalimide.

Among compounds from which anionic Q⁻ is derived, examples of active hydrogen compounds having active hydrogen atoms on sulfur atom include: monovalent thiols, including, for example, methanethiol, ethanethiol, normal-butanethiol, tertiary-butanethiol, hexanethiol, decanethiol, cyclopentyl mercaptan and cyclohexyl mercaptan; polyvalent thiols, including, for example, 1,2-ethanedithiol, 1,3-propanedithiol, 2,3-butanedithiol, 1,6-hexanedithiol, 1,2,3-propanetrithiol and 2,3-di(mercaptomethyl)-1,4-butanedithiol; aromatic mercapto compounds, including, for example, thiophenol, o-thiocresol, thionaphthol and 1,2-benzenedithiol.

The above described active hydrogen compounds contains compounds having plural active hydrogen atoms. In the plural active hydrogen atoms, all can be eliminated to form an anion, but part of the atoms can be eliminated to form an anion.

Furthermore, as anion Q⁻, any anion may be accepted so long as it does not hinder the process of the present invention.

Among compounds from which anionic Q⁻ is derived, examples of preferable compounds include: hydrogen halides, including, for example, hydrogen fluoride, hydrogen chloride, hydrogen bromide and hydrogen iodide; hydrogen cyanide, thiocyanic acid, water; carboxylic acids having 1 to 20 carbon atoms, including, for example, formic acid, acetic acid, propionic acid, butyric acid, isobutyric acid, lauric acid, stearic acid, oleic acid, phenylacetic acid, dihydrocinnamic acid, cyclohexanecarboxylic acid, benzoic acid, paramethylbenzoic acid and 2-carboxynaphthalene; alcohols having 1 to 20 carbon atoms, including, for example, methanol, ethanol, normal propanol, isopropanol, normal butyl alcohol, secondary butyl alcohol, tertiary butyl alcohol, isopentyl alcohol, tertiary pentyl alcohol, normal octyl alcohol, lauryl alcohol, cetyl alcohol, cyclopentanol, cyclohexanol, allyl alcohol, crotyl alcohol, methyl vinyl carbinol, benzyl alcohol, 1-phenylethyl alcohol, triphenyl carbinol and cinnamic alcohol; aromatic compounds having 6 to 20 carbon atoms and 1 to 3 hydroxyl group, including, for example, phenol, 2-naphthol, 2,6-dihydroxynaphthalene and bisphenol A; aliphatic or aromatic secondary amines having 2 to 20 carbon atoms, including, for example, dimethylamine, methyl ethylamine, diethylamine, di-nornal-propylamine, ethyl-normal-butylamine, methyl-secondary-butylamine, dipentylamine, dicyclohexylamine, N-methylaniline and diphenylamine; monovalent thiols, including, for example, methanethiol, ethanethiol, normal-butanethiol, tertiary-butanethiol, hexanethiol, decanethiol, cyclopentyl mercaptan and cyclohexyl mercaptan; aromatic mercapto compounds, including, for example, thiophenol, o-thiocresol, thionaphthol and 1,2-benzenedithiol.

More preferable compounds include: for example, hydrogen fluoride, hydrogen cyanide, thiocyanic acid, water; carboxylic acids having 1 to 20 carbon atoms, including, for example, formic acid, acetic acid, propionic acid, butyric acid, isobutyric acid, lauric acid, stearic acid, oleic acid, phenylacetic acid, dihydrocinnamic acid, cyclohexanecarboxylic acid, benzoic acid, paramethylbenzoic acid and 2-carboxynaphthalene; aromatic compounds having 6 to 20 carbon atoms and 1 to 3 hydroxyl group, including, for example, phenol, 2-naphthol, 2,6-dihydroxynaphthalene and bisphenol A; monovalent thiols, including, for example, methanethiol, ethanethiol, normal-butanethiol, tertiary-butanethiol, hexanethiol, decanethiol, cyclopentyl mercaptan and cyclohexyl mercaptan; aromatic mercapto compounds, including, for example, thiophenol, o-thiocresol, thionaphthol and 1,2-benzenedithiol.

Each of a, b, c and d in formula (1) (the same also in formula (2)) is 0 or 1. However, all of them are not to be 0 at the same time. It is preferable that at least three of a, b, c and d are 1. This means the numbers are in the combination of (1,1,1,1) or (0,1,1,1), regardless of the order. It is more preferable that all of a, b, c and d are 1.

R groups can be all the same or be different from each other in formula (1) (the same also in formula (2)). Two R groups in the expression of "$R_2$" may be different from each other. And R independently represents a hydrocarbon group having 1 to 10 carbon atoms, or two R groups on the same nitrogen atom can be bonded each other to form a ring together with the nitrogen atom.

When R singly represents a hydrocarbon group, it is selected from aliphatic or aromatic hydrocarbon groups, including, for example, methyl, ethyl, normal-propyl, isopropyl, allyl, normal-butyl, secondary-butyl, tertiary-butyl, 2-butenyl, 1-pentyl, 2-pentyl, 3-pentyl, 2-methyl-1-butyl, isopentyl, tertiary-pentyl, 3-methy-2-butyl, neopentyl, normal-hexyl, 4-methyl-2-pentyl, cyclopentyl, cyclohexyl, 1-heptyl, 3-heptyl, 1-octyl, 2-octyl, 2-ethyl-1-hexyl, 1,1-dimethyl-3,3-dimethylbutyl (a common name of tertiary-octyl), nonyl, decyl, phenyl, 4-toluic, benzyl, 1-phenylethyl and 2-phenylethyl. Among these groups, aliphatic hydrocarbon groups having 1 to 10 carbon atoms, including methyl, ethyl, normal-propyl, isopropyl, tertiary-butyl, tertiary-pentyl or 1,1-dimethyl-3,3-dimethylbutyl are preferable, and methyl group is more preferable.

In the case where two R groups are bonded together on the same nitrogen atom to form a ring and to become a divalent substituent, the main chain of the divalent substituent is preferable to be a divalent hydrocarbon group having 4 to 6 carbon atoms (the ring becomes a five to seven-membered ring), for example, tetramethylene, pentamethylene, hexamethylene and the like, or those in which an alkyl group like methyl, ethyl or the like is substituted on their main chains are preferable. Tetramethylene or pentamethylene is more preferable.

Either all or part of possible nitrogen atoms in a phosphazenium cation may be nitrogen atom having such a ring structure. When part of R groups forms a ring structure, remaining R groups can be the groups described above in the case where the R singly represents a hydrocarbon group, and preferable groups are also the same as those described.

These phosphazenium compounds can be synthesized by the method described in page 12 to 13 of EP 0791600, or by a method similar to the method.

A halogenated aromatic compound to be used in the present invention is a compound having at least one halogen atom on the aromatic ring, and it is either an aromatic hydrocarbon compound or an aromatic heterocyclic compound.

When a halogenated aromatic compound has a plurality of halogen atoms, it is sufficient that at least one of the atoms takes part in the substitution reaction to be substituted with Q. Moreover, an aromatic compound may have Q from the beginning, in such a case, after halogen is substituted with Q in the present process, there will be obtained such a compound that the number of Q is further increased by one or more.

Examples of halogenated aromatic hydrocarbon compounds include inactive fluorinated aromatic hydrocarbon compounds, inactive chlorinated aromatic hydrocarbon compounds, inactive brominated aromatic hydrocarbon compounds, inactive iodinated aromatic hydrocarbon compounds, active fluorinated aromatic hydrocarbon compounds, active chlorinated aromatic hydrocarbon compounds, active brominated aromatic hydrocarbon compounds and active iodinated aromatic hydrocarbon compounds.

Here, inactive and active halogenated aromatic hydrocarbon compounds are defined in accordance with the description in page 1298 to 1301 in "Organic Chemistry (the last volume; Japanese version)", 5th edition, written by R. T. Morrison and R. N. Boyd. That is, a halogenated aromatic hydrocarbon compound in which an electron-accepting group is substituted on o- and/or p-position to a halogen atom in a halogenated aromatic hydrocarbon compound is defined as an active halogenated aromatic hydrocarbon compound, and any compound other than that, that is, a halogenated aromatic hydrocarbon compound in which an electron-accepting group is not substituted on o- and/or p-position to a halogen atom in a halogenated aromatic hydrocarbon compound is defined as an inactive halogenated aromatic hydrocarbon compound.

Examples of inactive fluorinated aromatic hydrocarbon compounds include: fluorobenzene, 2-fluorotoluene, 3-fluorotoluene, 4-fluorotoluene, 2-methoxyfluorobenzene, 3-methoxyfluorobenzene, 4-methoxyfluorobenzene, 2-dimethylaminofluorobenzene, 3-dimethylaminofluorobenzene, 4-dimethylaminofluorobenzene, 2-hydroxyfluorobenzene, 3-hydroxyfluorobenzene, 4-hydroxyfluorobenzene, 2-aminofluorobenzene, 3-aminofluorobenzene, 4-aminofluorobenzene, 1,3-difluorobenzene, 1,3,5-trifluorobenzene, 3-nitrofluorobenzene, 3-cyanofluorobenzene, 3-phenylsulfonyl-fluorobenzene, 3-ethoxycarbonyl-fluorobenzene, 3-formylfluorobenzene, 3-phenylcarbonyl-fluorobenzene, 1-fluoronaphthalene, 2-fluoronaphthalene and the like.

Examples of inactive chlorinated aromatic hydrocarbon compounds include: chlorobenzene, 2-chlorotoluene, 3-chlorotoluene, 4-chlorotoluene, 2-methoxychlorobenzene, 3-methoxychlorobenzene, 4-methoxychlorobenzene, 2-dimethylaminochlorobenzene, 3-dimethylaminochlorobenzene, 4-dimethylaminochlorobenzene, 2-hydroxychlorobenzene, 3-hydroxychlorobenzene, 4-hydroxychlorobenzene, 2-aminochlorobenzene, 3-aminochlorobenzene, 4-aminochlorobenzene, 1,3-dichlorobenzene, 1,3,5-trichlorobenzene, 3-nitrochlorobenzene, 3-cyanochlorobenzene, 3-phenylsulfonyl-chlorobenzene, 3-ethoxycarbonyl-chlorobenzene, 3-formylchlorobenzene, 3-phenylcarbonyl-chlorobenzene, 1-chloronaphthalene, 2-chloronaphthalene and the like.

Examples of inactive brominated aromatic hydrocarbon compounds include: bromobenzene, 2-bromotoluene, 3-bromotoluene, 4-bromotoluene, 2-methoxybromobenzene, 3-methoxybromobenzene, 4-methoxybromobenzene, 2-dimethylaminobromobenzene, 3-dimethylaminobromobenzene, 4-dimethylaminobromobenzene, 2-hydroxybromobenzene, 3-hydroxybromobenzene, 4-hydroxybromobenzene, 2-aminobromobenzene, 3-aminobromobenzene, 4-aminobromobenzene, 1,3-dibromobenzene, 1,3,5-tribromobenzene, 3-nitrobromobenzene, 3-cyanobromobenzene, 3-phenylsulfonyl-bromobenzene, 3-ethoxycarbonyl-bromobenzene, 3-formylbromobenzene, 3-phenylcarbonyl-bromobenzene, 1-bromonaphthalene, 2-bromonaphthalene and the like.

Examples of inactive iodinated aromatic hydrocarbon compounds include: iodobenzene, 2-iodotoluene, 3-iodotoluene, 4-iodotoluene, 2-methoxyiodobenzene, 3-methoxyiodobenzene, 4-methoxyiodobenzene, 2-dimethylaminoiodobenzene, 3-dimethylaminoiodobenzene, 4-dimethylaminoiodobenzene, 2-hydroxyiodobenzene, 3-hydroxyiodobenzene, 4-hydroxyiodobenzene, 2-aminoiodobenzene, 3-aminoiodobenzene, 4-aminoiodobenzene, 1,3-diiodobenzene, 1,3,5-triiodobenzene, 3-nitroiodobenzene, 3-cyanoiodobenzene, 3-phenylsulfonyl-iodobenzene, 3-ethoxycarbonyl-iodobenzene, 3-formyliodobenzene, 3-phenylcarbonyl-iodobenzene, 1-iodonaphthalene, 2-iodonaphthalene and the like.

Examples of active fluorinated aromatic hydrocarbon compounds include: 2-nitrofluorobenzene, 4-nitrofluorobenzene, 2-cyanofluorobenzene, 4-cyanofluorobenzene, 2-phenylsulfonyl-fluorobenzene, 4-phenylsulfonyl-fluorobenzene, 4-ethoxycarbonyl-fluorobenzene, 4-formylfluorobenzene, 4-phenylcarbonyl-fluorobenzene, 2,4-dinitrofluorobenzene, 2-cyano-4-nitrofluorobenzene, 2,4-dicyanofluorobenzene, 1,2-difluorobenzene, 1,2,4-trifluorobenzene, hexafluorobenzene, 1,2-difluoronaphthalene, 1,2,4-trifluoronaphthalene, octafluoronaphthalene, 4,4'-difluorobenzophenone, 4,41'-difluorodiphenylsulfone and the like.

Examples of active chlorinated aromatic hydrocarbon compounds include: 2-nitrochlorobenzene, 4-nitrochlorobenzene, 2-cyanochlorobenzene, 4-cyanochlorobenzene, 2-phenylsulfonyl-chlorobenzene, 4-phenylsulfonyl-chlorobenzene, 4-ethoxycarbonyl-chlorobenzene, 4-formylchlorobenzene, 4-phenylcarbonyl-chlorobenzene, 2.4-dinitrochlorobenzene, 2-cyano-4-nitrochlorobenzene, 2,4-dicyanochlorobenzene, 1,2-dichlorobenzene, 1,2,4-trichlorobenzene, hexachlorobenzene, 1,2-dichloronaphthalene, 1,2,4-trichloronaphthalene, octachloronaphthalene, 4,4'-dichlorobenzophenone, 4,4'-dichlorodiphenylsulfone and the like.

Examples of active brominated aromatic hydrocarbon compounds include: 2-nitrobromobenzene, 4-nitrobromobenzene, 2-cyanobromobenzene, 4-cyanobromobenzene, 2-phenylsulfonyl-bromobenzene, 4-phenylsulfonyl-bromobenzene, 4-ethoxycarbonyl-bromobenzene, 4-formylbromobenzene, 4-phenylcarbonyl-bromobenzene, 2,4-dinitrobromobenzene, 2-cyano-4-nitrobromobenzene, 2,4-dicyanobromobenzene, 1,2-dibromobenzene, 1,2,4-tribromobenzene, hexabromobenzene, 1,2-dibromonaphthalene, 1,2,4-tribromonaphthalene, octabromonaphthalene, 4,4'-dibromobenzophenone, 4,4'-dibromodiphenylsulfone and the like.

Examples of active iodinated aromatic hydrocarbon compounds include: 2-nitroiodobenzene, 4-nitroiodobenzene, 2-cyanoiodobenzene, 4-cyanoiodobenzene, 2-phenylsulfonyl-iodobenzene, 4-phenylsulfonyl-iodobenzene, 4-ethoxycarbonyl-iodobenzene, 4-formyliodobenzene, 4-phenylcarbonyl-iodobenzene, 2,4-dinitroiodobenzene, 2-cyano-4-nitroiodobenzene, 2,4-dicyanoiodobenzene, 1,2-diiodobenzene, 1,2,4-triiodobenzene, hexaiodobenzene, 1,2-diiodonaphthalene, 1,2,4-triiodonaphthalene, octaiodonaphthalene, 4,4'-diiodobenzophenone, 4,4'-diiododiphenylsulfone and the like.

Aromatic heterocyclic compounds are, for example, fluorinated, chlorinated, brominated, or iodinated aromatic heterocyclic compounds.

Examples of fluorinated aromatic heterocyclic compounds include: 2-fluorofuran, 3-fluorofuran, 5-fluorofuraldehyde, 2-fluorothiophene, 3-fluorothiophene, 2,5-difluorothiophene, 3,4-difluorothiophene, tetrafluorothiophene, 2-acetyl-5-fluorothiophene, 3-acetyl-2,5-fluorothiophene, 4-fluoro-2-thiophenecarboaldehyde, 5-fluoro-2-thiophenecarboaldehyde, 4-fluoropyrazole, 4-fluoro-3-methylpyrazole, 5-fluoro-3-methyl-1-phenyl-4-pyrazolecarboaldehyde, 5-fluoro-1-methylimidazole, 2-fluorothiazole, 3,4-difluorothiazole, 4-fluoroindole, 5-fluoroindole, 5-fluoroindoleacetate, 2,4,8-trifluorobenzofuran, 2-fluorobenzimidazole, 5-fluorobenzotriazole, 5-fluoro-2-methylbenzoxazole, 2-fluoropyridine, 3-fluoropyridine, 2,5-difluoropyridine, 6-fluoropyridinol, 2-fluoro-5-nitropyridine, fluoropyrazine, 4-fluoro-quinoline, 6-fluoro-quinoline and the like.

As chlorinated aromatic heterocyclic compounds, compounds that fluorine atoms of the above described fluorinated aromatic heterocyclic compounds are replaced with chlorine atoms, dioxin and the like can be exemplified. As brominated aromatic heterocyclic compounds and iodinated aromatic heterocyclic compounds, compounds that fluorine atoms of the above described fluorinated aromatic heterocyclic compounds are replaced with bromine and iodine, respectively, can be exemplified.

In the above, although only such compounds that have one kind of halogen atom in the same molecule were illustrated on the convenience of the classification, halogenated aromatic compounds in the present invention are not limited to these illustrations, but may have 2 or more of different kinds of halogen atoms in the same molecule, and further these halogenated aromatic compounds can have any substituent, functional group, or heteroatom so long as the process of the present invention is impeded.

These halogenated aromatic compounds are preferably the above described inactive fluorinated aromatic hydrocarbon compounds, inactive chlorinated aromatic hydrocarbon compounds, inactive brominated aromatic hydrocarbon compounds, active fluorinated aromatic hydrocarbon compounds, active chlorinated aromatic hydrocarbon compounds, active brominated aromatic hydrocarbon compounds, chlorinated aromatic heterocyclic compounds or brominated aromatic heterocyclic compounds, and are more preferably inactive fluorinated aromatic hydrocarbon compounds, inactive chlorinated aromatic hydrocarbon compounds, inactive brominated aromatic hydrocarbon compounds, chlorinated aromatic heterocyclic compounds or brominated aromatic heterocyclic compounds. Further, inactive chlorinated aromatic hydrocarbon compounds, chlorinated aromatic heterocyclic compounds or brominated aromatic heterocyclic compounds are particularly preferred.

In the present invention, when Q is a halogen, a halogen that participate in the exchange reaction in an halogenated aromatic compound to be used in the reaction must be one that exists in the lower part in the periodic table than Q. That is, if Q⁻ is F⁻, for example, a usable halogenated aromatic compound is a halogenated aromatic compound having at least one of chlorine, bromine or iodine atom.

Consequently, if Q⁻ is F⁻, halogenated aromatic compounds are selected from the above described inactive or active, chlorinated, brominated or iodinated aromatic hydrocarbon compounds, and chlorinated, brominated or iodinated aromatic heterocyclic compounds and the like. Inactive chlorinated aromatic hydrocarbon compounds, inactive brominated aromatic hydrocarbon compounds, active chlorinated aromatic hydrocarbon compounds, active brominated aromatic hydrocarbon compounds, chlorinated aromatic heterocyclic compounds and brominated aromatic heterocyclic compounds are preferable, inactive chlorinated aromatic hydrocarbon compounds, inactive brominated aromatic hydrocarbon compounds, chlorinated aromatic heterocyclic compounds and brominated aromatic heterocyclic compounds are more preferable, and further inactive chlorinated aromatic hydrocarbon compounds, chlorinated aromatic heterocyclic compounds or brominated aromatic heterocyclic compounds are still more preferable.

The amount used of a phosphazenium compound represented by formula (1) is not especially limited, but the amount is usually 5 mol or less to 1 mol of the halogen atom to be substituted in a halogenated aromatic compound, and it is preferable to be 0.5 to 2 mol, and more preferable to be 0.8 to 1.2 mol.

The reaction temperature is not necessarily definite, depending on the kinds of a phosphazenium compound represented by formula (1) and a halogenated aromatic compound that are used, or of a solvent when used, but is usually 250° C. or less, preferably 0 to 230° C., and more preferably 30 to 200° C. The pressure during the reaction is not necessarily definite, depending on the kinds of raw materials and others to be used, but is usually 3.0 MPa (absolute pressure and the same in the description below) or less, preferably 0.01 to 1.5 MPa, and more preferably 0.1 to 1.0 MPa. The reaction time is usually within 48 hours, preferably 0.01 to 30 hours, and more preferably 0.02 to 15 hours.

Further, in one aspect of the present invention, when a substitution reaction with Q⁻ is carried out, a phosphazenium compound represented by formula (2)

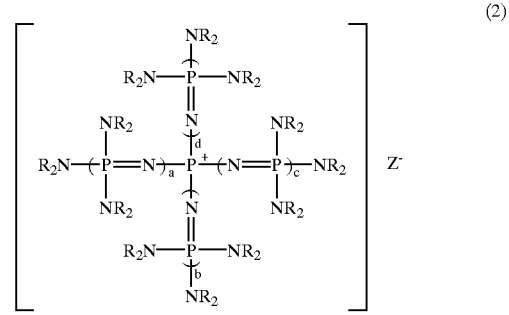

(in the formula, Z⁻ is a halogen anion, and a, b, c, d and R groups are the same meaning as described above) and a metal compound represented by $MQ_n$ (in the formula, M represents an alkaline metal atom, an alkaline earth metal atom, or a rare earth metal atom, Q is the same meaning as described above, and n is an integer from 1 to 3) are used as raw materials and made contact with each other to produce a phosphazenium compound represented by the above described formula (1) in the reaction system, and thus the above described substitution reaction can be carried out.

Here, conditions, preferable conditions and others concerned with a, b, c, d and R groups of a phosphazenium compound represented by formula (2) are the same as the conditions required for a, b, c, d and R groups in the above described formula (1).

Z⁻ is a halogen anion, for example, a fluorine anion, a chlorine anion, a bromine anion, an iodine anion or the like, and among them, a fluorine anion and chlorine anion are preferable, and a chlorine anion is more preferable.

In this reaction, when Q⁻ in [phosphazenium cation]⁺Q⁻ of formula (1) that was produced in the reaction system is consumed by reacting with an halogenated aromatic compound, Q is supplied from $MQ_n$. Consequently, there is such an advantage that the amount used of [phosphazenium cation]$^+$Z$^-$ of formula (2) is very little. Moreover, in the case where Z$^-$ is identical with Q$^-$, when Z$^-$(=Q$^-$) that has been fed previously is consumed, Q$^-$ is supplied from $MQ_n$, so there is also an advantageous effect even in the case where Z$^-$ is identical with Q$^-$.

Two or more kinds of these phosphazenium compounds represented by formula (2) may be used together. Further, a macrocyclic polyether (a crown ether and the like), a chain polyether, a quaternary ammonium salt, a quaternary phosphonium salt or the like, which have been conventionally used as catalysts, may be used together with these phosphazenium compounds represented by formula (2).

M in metal compounds represented by $MQ_n$ is a metal that can take the valence number up to trivalent.

Examples include: alkaline metal atoms, including, for example, lithium, sodium, potassium, cesium or rubidium; alkaline earth metal atoms, including, for example, magnesium, calcium, strontium or barium; rare earth metal atoms, including, for example, cerium, praseodymium, neodymium or samarium. Among them, alkaline metal atoms, including, for example, lithium, sodium, potassium, cesium or rubidium are preferable, and sodium and potassium are more preferable.

The n is an integer from 1 to 3, and is preferable to be 1.

The amount used of a phosphazenium compound represented by formula (2) is not especially limited. However, the amount can be enough to be lower than the number of moles of a halogen atom to be substituted in a halogenated aromatic compound. Therefore, the amount is usually 1 mol or less per 1 mol of the halogen atom to be substituted, and it is preferable in the range of 0.001 to 0.2 mol, and more preferable in the range of 0.01 to 0.1 mol.

Although the amount used of a metal compound $MQ_n$ is not especially limited, the number of moles of exchangeable Q in $MQ_n$ (usually n pieces of them can be exchanged) is usually in the range of 0.5 to 4.0 mol per 1 mol of the halogen atom to be substituted in the halogenated aromatic compound. It is preferably in the range of 0.8 to 2.5 mol, and more preferably in the range of 1.0 to 1.5 mol (the number of moles of $MQ_n$ is 1/n of these figures.).

The reaction temperature, the reaction pressure and the reaction time are the same as those when a phosphazenium compound of the above described formula (1) is used.

In the present invention, a reaction can be carried out without the use of a solvent. But a solvent can be used, if necessary, to ensure the effective contact of a phosphazenium compound represented by formula (1) or formula (2) with a halogenated aromatic compounds and a metal compound represented by $MQ_n$ in case it is present.

In this case, a solvent to be used is not necessarily definite, depending on the kind or the amount of these compounds to be used, but any solvent may be used so long as it does not hinder the reaction. The examples of solvents include aliphatic or aromatic hydrocarbons, including, for example, normal-pentane, normal-hexane, cyclohexane, benzene, toluene, xylene, tetralin, naphthalene, chlorobenzene, chlorotoluene, o-dichlorobenzene, 3, 4-dichlorotoluene and 1-chloronaphthalene; ethers, including, for example, diethyl ether, tetrahydrofuran, 1,4-dioxane, ethylene glycol dimethyl ether, triethylene glycol dimethyl ether, polyethylene glycol, polypropylene glycol and diphenyl ether; ketones, including, for example, acetone, methyl ethyl ketone, diisopropyl ketone and benzophenone; tertiary amines, including, for example, tributylamine, N,N-dimethylaniline, pyridine and quinoline; nitro compounds, including, for example, nitromethane, nitroethane, nitrobenzene and o-nitrotoluene; nitriles, including, for example, acetonitrile, propionitrile, 1,2-dicyanoethane and benzonitrile; aprotic polar solvents, including, for example, N,N-dimethylformamide, N-methylpyrrolidone, dimethyl sulfoxide, dimethyl sulfone, diphenyl sulfoxide, diphenyl sulfone, sulfolane, hexamethylphosphoric triamide and 1,3-dimethyl-2-imidazolidinone. These solvents may be used either alone or in a mixture of 2 or more kinds.

In the process of the present invention, a method of isolating an objective substituted aromatic compound from the reaction mixture is not necessarily definite, depending on the kind of used raw materials, the kind of the objective aromatic substituted compound or the kind and amount of a used solvent. But normally, the objective aromatic substituted compound can be obtained from the reaction mixture solution, or in the case where a solvent was used, from the reaction mixture after the solvent has been removed, by the use of any method of extraction, distillation, recrystalization, column chromatography or the like.

EXAMPLES

Example 1

After 7.71 g (10.0 mmol) of a phosphazenium compound, tetrakis[tris(dimethylamino)phosphoranylideneamino] phosphonium methoxide: [(Me$_2$N)$_3$P=N]$_4$P$^+$, MeO$^-$ was weighed into a 100 ml flask equipped with a thermometer under nitrogen atmosphere, 20.0 g (178 mmol) of chlorobenzene was added at room temperature. After the mixture was reacted at room temperature for 2 hours, a small volume of sample was taken from this reaction mixture and analyzed by gas chromatography. As a result, surprisingly in addition to the peak of chlorobenzene, a new peak was observed, which has a considerable integrated intensity. When GC-Mass (a mass spectrometry analyzer with gas chromatography) analysis of this reaction mixture was carried out, a molecular ion peak indicating methoxybenzene and a fragment ion peak indicating a phenyl group after the elimination of a methoxy group were detected at 108 and 77, respectively. This result shows that this new peak is methoxybenzene.

Again, this reaction operation was repeatedly carried out and the reaction mixture was obtained. A small volume of sample was taken from this reaction mixture and the quantitative analysis of methoxybenzene was carried out by gas chromatography with 1,2,3-trichlorobenzene as an internal standard. As a result, it was found that methoxybenzene was produced in the yield of 95%. Then, after the reaction mixture was washed by 20 ml of 1N hydrochloric acid solution and 20 ml of water, the separated organic phase liquid was distilled with a small precision distillation equipment and 0.961 g of objective methoxybenzene was obtained (yield of 89%). The measured charts of IR, $^1$H-NMR and $^{13}$C-NMR on this product accorded with those of the reference standard.

Example 2

After 7.59 g (10.0 mmol) of a phosphazenium compound, tetrakis[tris(dimethylamino)phosphoranylideneamino] phosphonium fluoride: [(Me$_2$N)$_3$P=N]$_4$P$^+$, F$^-$ was weighed into a pressure glass vessel having a volume of 100 ml and equipped with a thermometer under nitrogen atmosphere, 20.0 g (178 mmol) of chlorobenzene was added at room temperature and the vessel was sealed. This solution was heated to 130° C. and reacted at the temperature for 2 hours. After that, a small volume of sample was taken from the obtained reaction mixture and was quantitatively analyzed by gas chromatography similarly to Example 1. As a result, it was found that objective fluorobenzene was produced in the yield of 81%.

Example 3

The reaction was carried out in the same manner as in Example 1, except that the same molar amount of tetrakis[tris (dimethylamino)phosphoranylideneamino] phosphonium tert-butylthiolate: $[(Me_2N)_3P=N]_4P^+$, t-BuS$^-$ was used instead of tetrakis[tris(dimethylamino) phosphoranylideneamino]phosphonium methoxide in Example 1. Then, the quantitative analysis was carried out by similar gas chromatography. As a result, it was found that objective tert-butylphenyl thioether was produced in the yield of 99%.

Example 4

The reaction was carried out completely in the same manner as in Example 2, except that tetrakis[tris (dimethylamino)phosphoranylideneamino]phosphonium cyanide: $[(Me_2N)_3P=N]_4P^+$, CN$^-$ was used instead of tetrakis[tris(dimethylamino)phosphoranylideneamino] phosphonium fluoride in Example 2. It was found that objective benzonitrile was produced in the yield of 94%.

Example 5

The reaction was carried out completely in the same manner as in Example 2, except that tetrakis[tris (dimethylamino)phosphoranylideneamino]phosphonium thiocyanide: $[(Me_2N)_3P=N]_4P^+$, SCN$^-$ was used instead of tetrakis[tris(dimethylamino)phosphoranylideneamino] phosphonium fluoride in Example 2. It was found that objective phenyl isothiocyanate was produced in the yield of 90%.

Example 6

The reaction was carried out completely in the same manner as in Example 2, except that tetrakis[tris (dimethylamino)phosphoranylideneamino]phosphonium hydroxide: $[(Me_2N)_3P=N]_4P^+$, OH$^-$ was used instead of tetrakis[tris(dimethylamino)phosphoranylideneamino] phosphonium fluoride in Example 2, and the reaction temperature was changed to 150° C. It was found that objective phenol was produced in the yield of 41%.

Example 7

The reaction was carried out completely in the same manner as in Example 2, except that tetrakis[tris (dimethylamino)phosphoranylideneamino]phosphonium benzoate: $[(Me_2N)_3P=N]_4P^+$, $C_6H_5COO^-$ was used instead of tetrakis[tris(dimethylamino)phosphoranylideneamino] phosphonium fluoride in Example 2, and the reaction temperature was changed to 150° C. It was found that objective phenyl benzoate was produced in the yield of 31%.

Example 8

The reaction was carried out completely in the same manner as in Example 2, except that tetrakis[tris (dimethylamino)phosphoranylideneamino]phosphonium phenolate: $[(Me_2N)_3P=N]_4P^+$, $C_6H_5O^-$ was used instead of tetrakis[tris(dimethylamino)phosphoranylideneamino] phosphonium fluoride in Example 2, and the reaction temperature was changed to 160° C. It was found that objective diphenyl ether was produced in the yield of 61%.

Example 9

The reaction was carried out completely in the same manner as in Example 2, except that tetrakis[tris (dimethylamino)phosphoranylideneamino]phosphonium thiophenolate: $[(Me_2N)_3P=N]_4P^+$, $C_6H_5S^-$ was used instead of tetrakis[tris(dimethylamino) phosphoranylideneamino]phosphonium fluoride and using 4-chlorotoluene was used instead of chlorobenzene in Example 2, and the reaction temperature was changed to 160° C. It was found that objective 4-phenylthiotoluene was produced in the yield of 88%.

Example 10

The reaction was carried out completely in the same manner as in Example 1, except that tetrakis[tris (dimethylamino)phosphoranylideneamino]phosphonium di-normal-propylamide: $[(Me_2N)_3P=N]_4P^+$, $(C_3H_7)_2N^-$ was used instead of tetrakis[tris(dimethylamino) phosphoranylideneamino]phosphonium methoxide in Example 1. It was found that objective di-normal-propylamino benzene was produced in the yield of 91%.

Example 11

The reaction was carried out completely in the same manner as in Example 2, except that 1,2-dichlorobenzene was used instead of chlorobenzene in Example 2. Objective 2-chlorofluorobenzene was produced in the yield of 92%.

Example 12

The reaction was carried out completely in the same manner as in Example 2, except that 1,3-dichlorobenzene was used instead of chlorobenzene in Example 2. Objective 3-chlorofluorobenzene was produced in the yield of 74%.

Example 13

The reaction was carried out completely in the same manner as in Example 2, except that 1,3-dibromobenzene was used instead of chlorobenzene in Example 2. Objective 3-bromofluorobenzene was produced in the yield of 85%.

Example 14

The reaction was carried out completely in the same manner as in Example 2, except that 3-chlorofluorobenzene was used instead of chlorobenzene in Example 2. Objective 1,3-difluorobenzene was produced in the yield of 77%.

Example 15

The reaction was carried out completely in the same manner as in Example 1, except that 1,3-dichlorobenzene was used instead of chlorobenzene in Example 1. Objective 3-chloroanisole was produced in the yield of 92%.

Example 16

The reaction was carried out completely in the same manner as in Example 1, except that tris[tris (dimethylamino)phosphoranylideneamino](dioctylamino) phosphoranylideneamino phosphonium ethoxide: $[(Me_2N)_3P=N]_3P^+\{N=P[N(C_8H_{17})_2]\}$, $C_2H_5O^-$ was used instead of tetrakis[tris(dimethylamino) phosphoranylideneamino]

phosphonium methoxide in Example 1. Objective ethoxybenzene was produced in the yield of 86%.

Example 17

After 7.71 g (10.0 mmol) of tetrakis[tris(dimethylamino) phosphoranylideneamino]phosphonium methoxide was weighed into a pressure glass vessel having a volume of 100 ml and equipped with a thermometer, 30 ml of anhydrous tetrahydrofuran (hereafter, it will be abbreviated as THF)and 1.66 g (10.0 mmol) of 1-methyl-6-chloroindole were added at room temperature. After the mixture was reacted at room temperature for 16 hours, a small volume of sample was taken from this reaction mixture and was analyzed by gas chromatography. It was found that objective 1-methyl-6-methoxyindole was produced in the yield of 89%.

Example 18

The reaction was carried out completely in the same manner as in Example 17, except that 2.5 times molar amount of tetrakis[tris(dimethylamino) phosphoranylideneamino]phosphonium fluoride was used instead of tetrakis[tris(dimethylamino) phosphoranylideneamino]phosphoniummethoxide and the same molar amount of 1,2-dichlorobenzene was used instead of 1-methyl-6-chloroindole in Example 17, and the reaction temperature was changed to 130° C. Objective 1,2-fluorobenzene was produced in the yield of 92%.

Example 19

The reaction was carried out completely in the same manner as in Example 17, except that 2.5 times molar amount of tetrakis[tris(dimethylamino) phosphoranylideneamino]phosphonium fluoride was used instead of tetrakis[tris(dimethylamino) phosphoranylideneamino]phosphonium methoxide, an equimolecular amount of 4,4'-dichlorobenzophenone was used instead of 1-methyl-6-chloroindole and toluene was used instead of THF in Example 17. Further, the reaction temperature was changed to 70° C. Objective 4,4'-difluorobenzophenone was produced in the yield of 99%.

Example 20

The reaction was carried out completely in the same manner as in Example 17, except that tetrakis[tris (dimethylamino)phosphoranylideneamino]phosphonium fluoride was used instead of tetrakis[tris(dimethylamino) phosphoranylideneamino]phosphonium methoxide, 4-bromopyridine was used instead of 1-methyl-6-chloroindole and toluene was used instead of THF in Example 17. Further, the reaction temperature was changed to 130° C. Objective 4-fluoropyridine was produced in the yield of 89%.

Example 21

Into a 100-ml flask equipped with a thermometer and a condenser, 2.36 g (15.0 mmol) of p-chloronitrobenzene, 1.31 g (22.5 mmol) of potassium fluoride (a compound corresponding to $MQ_n$) produced by the spray-dry method by Wako Pure Chemical Industries, Ltd., 0.55 g (0.75 mmol) of a tetrakis[tris(dimethylamino)phosphoranylideneamino] phosphonium chloride: $[(Me_2N)_3P=N]_4P^+,Cl^-$, which is phosphazenium compound, that had been sufficiently dried by circulating dry nitrogen at 100° C., and 10.4 g of anhydrous dimethylsulfoxide (hereafter, it is abbreviated as DMSO) were fed under nitrogen atmosphere. This suspension was heated to 150° C. in about 10 minutes while stirring. Then, after 30 minutes, after 1 hour, after 3 hours and after 6 hours, small volume of samples were taken from the reaction mixture and were quantitatively analyzed by gas chromatography similarly to Example 1.

As a result, it was found that the production yields of p-fluoronitrobenzene corresponding to each reaction time were 33%, 50%, 83% and 98%. After that, the reaction mixture was cooled to room temperature and insoluble solids were separated by filtering. These solids were washed two times by 10 ml of toluene, and the washings were mixed with the mother layer. After this solution was washed 3 times by 50 ml of water, the organic phase was dried with sodium sulfate and then toluene was removed by distillation under reduced pressure. As a result, 1.87 g of nearly pure p-fluoronitrobenzene was obtained as an oily substance.

Even if a phosphazenium compound was used in such a small amount as that of a catalyst, a substitution reaction was progressed by using together a compound corresponding to $MQ_n$, and more surprisingly, it was found that the reaction speed of producing p-fluoronitrobenzene was increased 12 times or more compared to the reaction speed under non-catalytic conditions shown in Comparative example 1 and further increased about 10 times compared to the reaction speed when a conventional catalyst shown in Comparative example 2 or 3 was used. These results are shown in FIG. 1.

Comparative Example 1

The reaction and the quantitative analysis was carried out in the same manner as in Example 21, except that a phosphazenium compound, tetrakis[tris(dimethylamino) phosphoranylideneamino]phosphonium chloride in Example 21 was not used. The production yields of p-fluoronitrobenzene after 30 minute, after 1 hour, after 3 hours and after 6 hours were 4%, 7%, 15% and 24%, respectively.

Comparative Example 2

The reaction and the quantitative analysis was carried out in the same manner as in Example 21, except that the same molar amount of tetraphenylphosphonium bromide was used instead of a phosphazenium compound, tetrakis[tris (dimethylamino)phosphoranylideneamino]phosphonium chloride in Example21. The production yields of p-fluoronitrobenzene after 30 minute, after 1 hour, after 3 hours and after 6 hours were 6%, 12%, 27% and 38%, respectively.

Comparative Example 3

The reaction and the quantitative analysis was carried out in the same manner as in Example 21, except that the same molar amount of 18-crown-6 was used instead of a phosphazenium compound, tetrakis[tris(dimethylamino) phosphoranylideneamino]phosphonium chloride in Example21. The production yields of p-fluoronitrobenzene after 30 minute, after 1 hour, after 3 hours and after 6 hours were 5%, 11%, 23% and 34%, respectively.

Example 22

The reaction was carried out completely in the same manner as in Example 21, except that p-fluoronitrobenzene was used instead of p-chloronitrobenzene and sodium phenolate was used instead of potassium fluoride in Example 21. Further, the reaction temperature was changed to 80° C. and the reaction time was changed to 3 hours without pursuing the reaction on halfway. Objective 4-phenoxynitrobenzene was produced in the yield of 98%.

Example 23

The reaction was carried out completely in the same manner as in Example 21, except that hexabromobenzene was used instead of p-chloronitrobenzene, changing the amount used of potassium fluoride to 3 times molar amount and 1,3-dimethyl-2-imidazolidinone was used instead of DMSO in Example 21. Further, the reaction temperature was changed to 200° C. and the reaction time was changed to 9 hours without pursuing the reaction on halfway. Objective 1,3,5-trifluoro-2,4,6-tribromobenzene was produced in the yield of 85%.

Example 24

The reaction was carried out completely in the same manner as in Example 1, except that tris[tris(dimethylamino)phosphoranylideneamino](dimethylamino) phosphonium ethoxide: [(Me$_2$N)$_3$P=N]$_3$P$^+$(NMe$_2$), C$_2$H$_5$O$^-$ was used instead of tetrakis[tris(dimethylamino) phosphoranylideneamino]phosphonium methoxide in Example 1. Objective ethoxybenzene was produced in the yield of 66%.

INDUSTRIAL APPLICABILITY

According to the process of the present invention, the nucleophilic substitution reaction of a halogenated aromatic compound, especially an chlorinated aromatic compound that is industrially easily producible and easily available, can be carried out under milder conditions than those in conventional methods to produce an objective substituted aromatic compound in a high yield.

What is claimed is:

1. A process for preparation of a substituted aromatic compound substituted with Q, which comprises:

reacting a phosphazenium compound represented by formula (1)

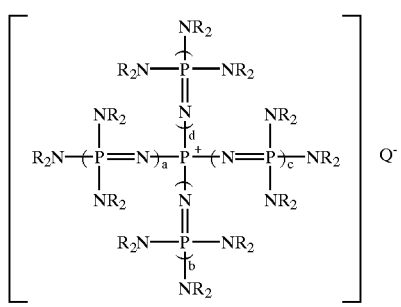

(1)

(in the formula,

Q$^-$ represents an anion in a form derived by elimination of a proton from an inorganic acid, or an active hydrogen compound having an active hydrogen on an oxygen atom, a nitrogen atom or a sulfur atom;

a, b, c and d, each independently, is 0 or 1, but all of them are not 0 simultaneously; and R groups represent the same or different hydrocarbon groups having 1 to 10 carbon atoms, or two Rs on each common nitrogen atom may be bonded together to form a ring structure) with a halogenated aromatic compound having halogen atoms;

whereby, at least one halogen atom in the halogenated aromatic compound is substituted with Q (where, Q represents an inorganic group or an organic group in a form derived by elimination of one electron from Q$^-$ in formula (1)).

2. A process according to claim 1, wherein:

a phosphazenium compound represented by formula (2)

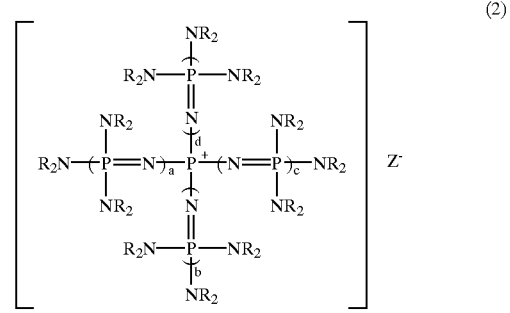

(2)

(in the formula, Z$^-$ is a halogen anion, and a, b, c, d and R groups are the same meaning as described above) and a metal compound represented by MQ$_n$ (in the formula, M represents an alkaline metal atom, an alkaline earth metal atom, or a rare earth metal atom, Q is the same meaning as described above, and n is an integer from 1 to 3) are used as raw materials and made contact with each other to produce a phosphazenium compound represented by the formula (1) in the reaction system; whereby, at least one halogen atom in the halogenated aromatic compound is substituted with Q.

3. A process according to claim 1, wherein at least three of a, b, c and d are 1.

4. A process according to claim 2, wherein at least three of a, b, c and d are 1.

5. A process according to claim 1, wherein all of the R groups are the same or different aliphatic hydrocarbon groups having 1 to 10 carbon atoms.

6. A process according to claim 2, wherein all of the R groups are the same or different aliphatic hydrocarbon groups having 1 to 10 carbon atoms.

7. A process according to claim 5, wherein all of the R groups are a methyl group.

8. A process according to claim 6, wherein all of the R groups are a methyl group.

9. A process according to claim 1, wherein among at least part of the R groups, two R groups on the same nitrogen atom are bonded to each other to form a ring structure; the divalent substituent formed by the bond of the two R groups being tetramethylene or pentamethylene.

10. A process according to claim 2, wherein among at least part of the R groups, two R groups on the same nitrogen atom are bonded to each other to form a ring structure; the divalent substituent formed by the bond of the two R groups being tetramethylene or pentamethylene.

11. A process according to claim 1, wherein a compound from which Q$^-$ in formula (1) is derived is one of hydrogen halides, hydrogen cyanide, thiocyanic acid, water, carboxylic acids having 1 to 20 carbon atoms, alcohols having 1 to 20 carbon atoms, aromatic compounds having 6 to 20 carbon atoms and 1 to 3 hydroxyl groups, aliphatic or aromatic secondary amines having 2 to 20 carbon atoms, monovalent thiols and aromatic mercapto compounds.

12. A process according to claim 2, wherein a compound from which Q$^-$ in formula (1) and Q in MQ$_n$ are derived is one of hydrogen halides, hydrogen cyanide, thiocyanic acid, water, carboxylic acids having 1 to 20 carbon atoms, alcohols having 1 to 20 carbon atoms, aromatic compounds having 6 to 20 carbon atoms and 1 to 3 hydroxyl groups, aliphatic or aromatic secondary amines having 2 to 20 carbon atoms, monovalent thiols and aromatic mercapto compounds.

13. A process according to claim 1, wherein when $Q^-$ in formula (1) is not $F^-$, the halogenated aromatic compound is inactive fluorinated aromatic hydrocarbon compound, inactive chlorinated aromatic hydrocarbon compound, inactive brominated aromatic hydrocarbon compound, active fluorinated aromatic hydrocarbon compound, active chlorinated aromatic hydrocarbon compound, active brominated aromatic hydrocarbon compound, chlorinated aromatic heterocyclic compound or brominated aromatic heterocyclic compound.

14. A process according to claim 2, wherein when $Q^-$ in formula (1) and Q in $MQ_n$ are not $F^-$ and F, respectively, the halogenated aromatic compound is inactive fluorinated aromatic hydrocarbon compound, inactive chlorinated aromatic hydrocarbon compound, inactive brominated aromatic hydrocarbon compound, active fluorinated aromatic hydrocarbon compound, active chlorinated aromatic hydrocarbon compound, active brominated aromatic hydrocarbon compound, chlorinated aromatic heterocyclic compound or brominated aromatic heterocyclic compound.

15. A process according to claim 1, wherein when $Q^-$ in formula (1) is $F^-$, the halogenated aromatic compound is inactive chlorinated aromatic hydrocarbon compound, inactive brominated aromatic hydrocarbon compound, active chlorinated aromatic hydrocarbon compound, active brominated aromatic hydrocarbon compound, chlorinated aromatic heterocyclic compound or brominated aromatic heterocyclic compound.

16. A process according to claim 2, wherein when $Q^-$ in formula (1) and Q in $MQ_n$ are $F^-$ and F, respectively, the halogenated aromatic compound is inactive chlorinated aromatic hydrocarbon compound, inactive brominated aromatic hydrocarbon compound, active chlorinated aromatic hydrocarbon compound, active brominated aromatic hydrocarbon compound, chlorinated aromatic heterocyclic compound or brominated aromatic heterocyclic compound.

17. A process according to claim 2, wherein M in $MQ_n$ is an alkaline metal atom.

* * * * *